US00PP21407P2

(12) United States Plant Patent
O'Connell

(10) Patent No.: US PP21,407 P2
(45) Date of Patent: Oct. 19, 2010

(54) ***AEONIUM* PLANT NAMED 'MARDI GRAS'**

(50) Latin Name: *Aeonium hybrid*
Varietal Denomination: Mardi Gras

(76) Inventor: Renee O'Connell, 1801 Tierra Libertia, Escondido, CA (US) 92026

( * ) Notice: Subject to any disclaimer, the term of this patent is extended or adjusted under 35 U.S.C. 154(b) by 0 days.

(21) Appl. No.: 12/455,720

(22) Filed: Jun. 6, 2009

(51) Int. Cl.
*A01H 5/00* (2006.01)

(52) U.S. Cl. ..... Plt./373

(58) Field of Classification Search ..... Plt./373
See application file for complete search history.

*Primary Examiner*—Annette H Para

(57) ABSTRACT

A new and distinct *Aeonium* cultivar named 'Mardi Gras' is disclosed, characterized a unique, stable tricolor variegation, incorporating lemon yellow, green and burgundy. Plants are compact, and very suitable for production in smaller pot sizes, such as a commercial 4 inch nursery container. 'Mardi Gras' shows very little negative effects under low water stress, instead foliage makes a very attractive burgundy blush. The new variety is an *Aeonium*, typically produced as a garden or container plant.

1 Drawing Sheet

Figure 1:
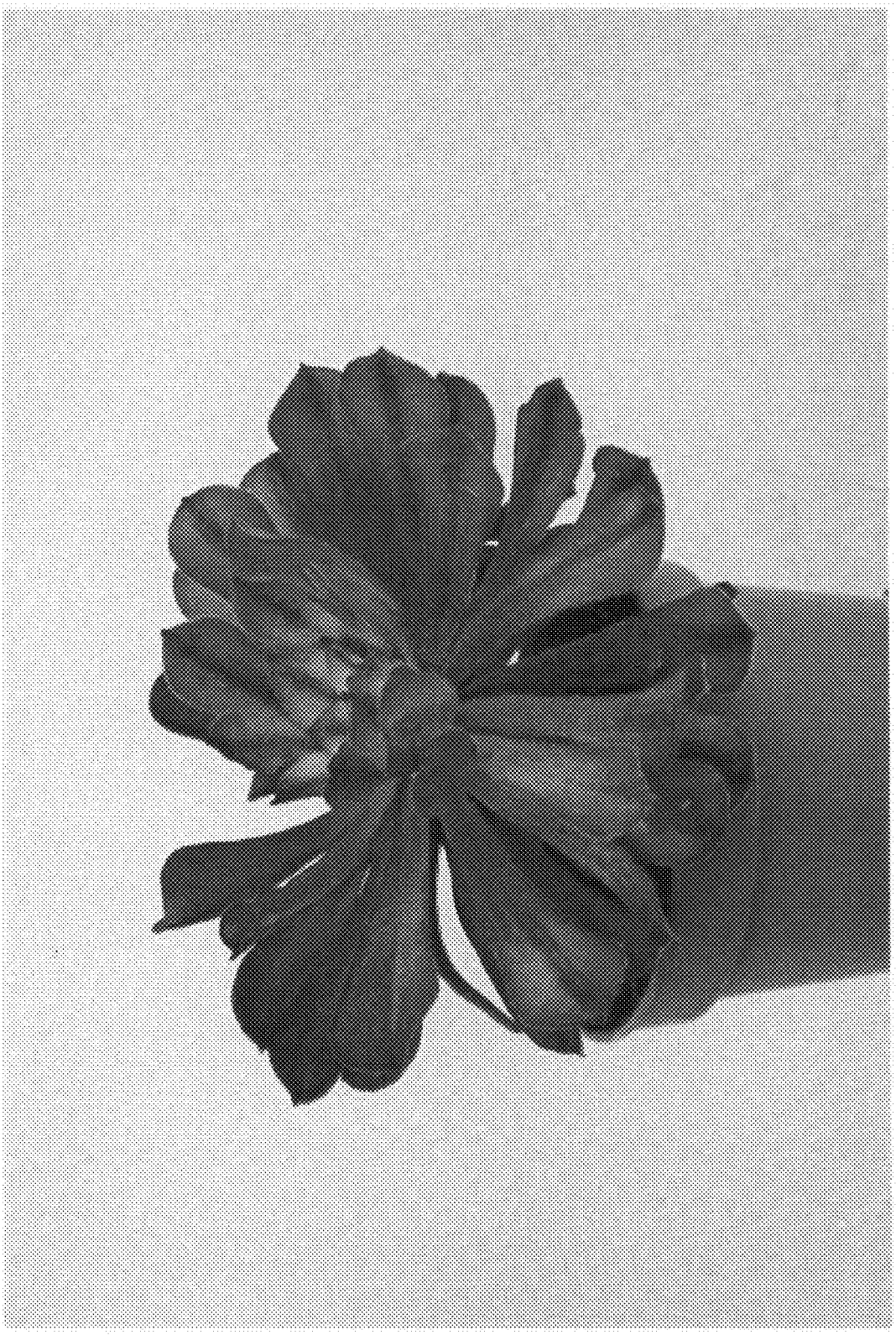

Latin name of the genus and species: *Aeonium* hybrid.
Variety denomination: 'Mardi Gras'.

BACKGROUND OF THE INVENTION

The new cultivar is a product of a planned breeding program. The new variety originated from a cross pollination of the seed parent, an unpatented proprietary selection of *Aeonium* hybrid referred to as '#13' with the pollen parent and unpatented commercial vareity, *Aeonium* hybrid 'Velour.' The crossing was made during March of 2007 in Vista, Calif., at a commercial greenhouse. 'Mardi Gras' was discovered by the inventor, Renee O'Connell, in October of 2007, in Vista, Calif. at a commercial greenhouse.

Asexual reproduction of the new cultivar 'Mardi Gras' was first performed in Vista, Calif., at a commercial greenhouse by vegetative leaf cuttings in October 2007. 'Mardi Gras' has since produced several generations and has shown that the unique features of this cultivar are stable and reproduced true to type.

SUMMARY OF THE INVENTION

The cultivar 'Mardi Gras' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Mardi Gras.' These characteristics in combination distinguish 'Mardi Gras' as a new and distinct *Aeonium* cultivar:

1. Unique tricolor variegated foliage.
2. Unusual lemon yellow with green and pink blush foliage.
3. Intense deep burgundy foliage color during times of drought or cold.

PARENTAL COMPARISON

Plants of the new cultivar 'Mardi Gras' are similar to the female parent '#13' in most horticultural characteristics.

However, 'Mardi Gras' differs in producing more compact plant, with tricolor foliage, whereas the seed parent does not have tri-color foliage, and has no lemon yellow coloration of its foliage.

Plants of the new cultivar 'Mardi Gras' are similar to the male parent 'Velour' in most horticultural characteristics. However, 'Mardi Gras' differs in having tricolor foliage, whereas the pollen parent does not have tri-color foliage, and has no lemon yellow coloration of its foliage.

COMMERCIAL COMPARISON

'Mardi Gras' can be compared to the unpatented commercial variety *Aeonium arboreum* 'Tricolor.' Plants of *Aeonium arboreum* 'Tricolor' are similar to plants of 'Mardi Gras' in most horticultural characteristics, however, 'Mardi Gras' produces more sideshoots, a more compact plant and a different tri color variegation combination. Additionally, 'Mardi Gras' maintains a more stable foliage coloration than *Aeonium arboreum* Tricolor.

'Mardi Gras' can also be compared to the unpatented commercial variety *Aeonium* 'Sunburst.' Plants of *Aeonium* 'Sunburst' are similar to plants of 'Mardi Gras' in most horticultural characteristics, however, 'Mardi Gras' produces a significantly more compact plant and has foliage that produces a deep burgundy blush under drought or cold conditions. Additionally, 'Mardi Gras' maintains a more stable foliage coloration than *Aeonium* 'Sunburst'.

BRIEF DESCRIPTION OF THE PHOTOGRAPH

The accompanying photograph in FIG. 1 illustrates in full color a typical plant of 'Mardi Gras' grown outdoors in Vista, Calif. This plant is approximately 4 months old, shown in a 4 inch pot. Plants were produced under some low water stress, to induce the burgundy blush coloration mentioned as a distinctive characteristic. The photograph was taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, except where general terms of ordinary dictionary significance are used. The following observations and measurements describe 'Mardi Gras' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Plants were produced under some low water stress, to induce the burgundy blush coloration mentioned as a distinctive characteristic. Measurements and numerical values represent averages of typical plant types.

Botanical classification: *Aeonium hybrid* 'Mardi Gras'.
Age of the plant described: Approximately 4 months.
Container size of the plant described: 4 inch.

PROPAGATION

Time to initiate roots: About 15 days at approximately 21° C.
Root description: Fibrous.
Propagation method: Vegetative divisions.

PLANT

Growth Habit: Compact succulent, producing foliage in a rosulate pattern.
Container size: 4 inch.
Height: Approximately 10.5 cm to top of highest leaf.
Plant spread: Approximately 16.5 cm.
Growth rate: Moderate.
Branching characteristics: Produces offsets from outer ring of main rosette.

FOLIAGE

Leaf:

*Arrangement.*—Densely rosulate.
*Average length.*—Approximately 7 cm.
*Widest width.*—Approximately 2 cm.
*Width at base.*—Approximately 0.5 cm.

FOLIAGE

Leaf:

*Shape of blade.*—Spatulate.
*Apex.*—Mucronate.
*Base.*—Rounded.
*Margin.*—Denticulate to serrulate.
*Texture of top surface.*—Glabrous.
*Texture of bottom surface.*—Glabrous.
*Quantity of leaves per plant.*—Approximately 75.
*Color.*—Young foliage upper side: Rose color near S 147-1 Pantone, yellow color near S 26-7 Pantone and apple green color near S 297-3 Pantone. Young foliage, upper side: Margin near tip near S 143-4 to S 144-1 Pantone. Young foliage under side: Near S 144-4; yellow color near S 5-5 to S 5-7 Pantone. Mature foliage upper side: Rose color near S 134-3, odd bronze green color where overlaid with rose near S 320-9 Pantone. Mature foliage under side: Near S 136-3, S 15-6, S 292-7 other green Pantone.
*Venation.*—Type: Parallel. Venation color upper side: Near S 155-2 Pantone. Venation color under side: Near S 155-2 Pantone.

FLOWER

Flower has not yet been observed to date.

OTHER CHARACTERISTICS

Seeds and fruits: Not observed to date.
Disease/pest resistance: Neither resistance nor susceptibility to normal diseases and pests of *Aeonium* has been observed.
Temperature tolerance: Tolerates temperatures from approximately −1 C. to 32 C.
Drought tolerance: Tolerates at least 2 weeks of high temperatures without supplemental water, showing no serious damage to plant.

What is claimed is:

1. A new and distinct cultivar of *Aeonium* plant named 'Mardi Gras' as herein illustrated and described.

* * * * *